US006997399B2

(12) United States Patent
Lacy

(10) Patent No.: US 6,997,399 B2
(45) Date of Patent: Feb. 14, 2006

(54) HYDRAULIC POWERED SPRAYING SYSTEM FOR HOME GARDENS

(76) Inventor: Jack Lacy, 2320-C Grants Cir., Richmond, VA (US) 23233

( * ) Notice: Subject to any disclaimer, the term of this patent is extended or adjusted under 35 U.S.C. 154(b) by 392 days.

(21) Appl. No.: 10/305,574

(22) Filed: Nov. 26, 2002

(65) Prior Publication Data

US 2003/0098315 A1 May 29, 2003

Related U.S. Application Data

(60) Provisional application No. 60/333,320, filed on Nov. 26, 2001.

(51) Int. Cl.
*A61M 11/02* (2006.01)

(52) U.S. Cl. ....................... 239/373; 239/375; 239/327; 239/310; 239/322; 239/378; 222/386

(58) Field of Classification Search ................. 239/323, 239/327, 310, 373, 375, 378, 322, 356, 362; 169/73; 222/386, 94, 95
See application file for complete search history.

(56) References Cited

U.S. PATENT DOCUMENTS 1,743,056 A * 1/1930 Whitaker ..................... 141/27
2,865,541 A * 12/1958 Hicks ...................... 222/386.5
3,720,230 A * 3/1973 Stockstill ................. 137/564.5
3,933,415 A * 1/1976 Woolpert .................... 401/145
5,499,750 A * 3/1996 Manifold ................. 222/386.5
6,595,392 B2 * 7/2003 Barnett ....................... 222/105

* cited by examiner

*Primary Examiner*—Dinh Q. Nguyen
(74) *Attorney, Agent, or Firm*—Law Offices of Royal W. Craig

(57) ABSTRACT

A spraying system for the application of fertilizer, insecticides, fungicides, etc. to plants, vegetables, small trees and lawns. The spraying system presents several improvements over the original Lacy Sprayer (see U.S. Pat. No. 5,398,852) inclusive an improved bladder attachment and improved bladder design, and a new pressure-limiting flow restrictor to ensure safe operation, and a spray discharge fitting incorporating a porous filter to protect the bladder from excessive stresses. The spray hose is connected to this assembly. The improved system facilitates a method of use in which the tank containing the spray solution is placed stationery in an area to be sprayed. The operator attaches a long (30'+ or −) small diameter spray hose for remote spraying within a radius permitted by the spray hose. The spraying system avoids the need to pump or to carry a heavy tank while spraying. Moreover, the continuous, higher pressure of the spraying system provides a wide range of operation from a foggy mist to spraying the tops of good size trees, and saves more than half the spray solution normally wasted.

16 Claims, 9 Drawing Sheets

HYDRAULIC POWERED SPRAYING SYSTEM FOR HOME GARDENS

CROSS-REFERENCE TO RELATED APPLICATION

The present application derives priority from U.S. Provisional Patent Application No. 60/333,320 for "HYDRAULIC POWERED SPRAYING SYSTEM FOR HOME GARDENS" filed 26 Nov. 2001.

BACKGROUND OF THE INVENTION

1. Field of the Invention

The present invention relates to pressurized sprayers for the application of fertilizer, insecticides, fungicides, etc. to plants, vegetables, trees and lawns, that permits the tank containing the spray solution to be set in one spot central to the area to be sprayed. The operator then uses a small diameter spray hose attached to said tank to spray within the radius permitted by the length of the long (30'+ or −) spray hose.

2. Description of the Background

There are many pressurized liquid spraying devices that are presently available on the market. Such sprayers range from back-pack sprayers that pump the liquid directly as it is being dispensed, to gasoline or electric powered sprayers for commercial use. Compressed air pump-sprayers are the common denominator for home gardens and are found in garden and hardware stores for spraying small amounts of liquid chemical solution from a tank under pressure. A hand pump is used to supply air pressure to the inside of the tank to pressurize the liquid to be dispensed from the tank, the pressure declines and it is necessary that the hand pump be repeatedly operated to rebuild the pressure. These sprayers are convenient inasmuch as they are completely portable, but they are constantly in need of pumping and must be carried while in use. Alternatively, the powered commercial sprayers never need pumping and are well suited for spraying a wide area efficiently. However, these are usually large devices on wheels, pulled by hand or tractor, expensive, and are not well suited for small gardens.

U.S. Pat. No. 5,398,852 to the present inventor discloses a unitary pressurizing tank with a cap (Lacy Cap) that connects to a standard garden hose and uses household water pressure to pressurize the tank's contents. The cap includes a flexible bladder for insertion into the tank. The cap further includes a handle that can be used for carrying the tank and providing access to inside of the bladder. This type of sprayer is much easier to use since it never needs pumping. In addition, it can be moved to any location accessible to a garden hose for easy spraying. The greatly improved efficiency of this spraying system results from the introduction of two synergistic factors not found in the conventional compressed air sprayers: (1) a fixed, continuously maintained pressure allowing the operator to set the spray to precisely produce the best spray for that particular requirement, and (2) the probability that the pressure at the nozzle will be approximately two to three times higher (23# avg. vs. 50 to 80#), permitting a further reduction in droplet size and the consequent greater coverage. The overall increase in coverage may be as much as four times that of conventional equipment.

However, the '852 sprayer does leave room for improvement in it's design and construction in four ways: (a) design of the attachment of the pressurizing bladder to the cap; (b) means to safely manage the excess water supply and/or pressure; (c) ease of application of the spray to garden and foliage by reducing the necessity of moving the spray tank; and (d) design of a pressurizing bladder to prevent said bladder from sealing off the discharge assembly, thereby preventing flow of spray solution into the spray hose.

SUMMARY OF THE INVENTION

It is, therefore, an object of the present invention to provide a semi-portable spraying system based on the Lacy sprayer as shown and described in his U.S. Pat. No. 5,398,852, and yet which employs a stationary water-pressurized base and remote hose-connected spray head for more convenient wide-area spraying.

It is another object to incorporate a number of structural improvements into the water-pressurized base for greater suitability to task, and specifically an improved bladder retaining neck structure as well as a pressure-limiting O-ring to compensate for water systems of varying pressures.

According to the present invention, the above-described and other objects are accomplished by providing a spraying system inclusive of a tank reservoir and pressure cap attached thereto. The pressure cap has a coupling for a garden hose to pressurize the tank. The pressure cap further comprises a handle assembly having a lower portion for attachment to the cap body, a lateral aperture for attachment of the water hose, and a second aperture for attachment of a pressure relief valve. In addition, a body insert is attachable to the cap body to provide a passage for the pressurizing water to the bladder and for supporting the bladder. To mount the bladder for use, the mouth of the bladder is pulled onto the body insert to a point approximately ½ inch above the flange. An O-ring is slipped down over that portion of the body insert and over the top of the bladder, and is seated on the flange of the body insert. The top of the bladder is pulled down over and outside the O-ring. A cuff ring is slipped down over the O-ring and a cuff ring nut is screwed down to hold the cuff ring in position. The completed body insert assembly is then attached to the cap body. The foregoing simplifies the bladder attachment structure and greatly increases the integrity thereof.

A flow restrictor orifice is positioned in a lateral aperture of the handle assembly for limiting the flow rate of water from the water hose to a flow rate commensurate with the flow capacity of the relief valve on the opposite side of the handle. Consequently, the spraying system is operable over a broad range of pressures and flow rates.

The foregoing facilitates an improved method of using the spraying system comprising the steps of placing the spraying system stationary on the ground, attaching an elongate spraying hose to the tank at a point near the tank bottom, and extending the spraying hose for remote spraying at a distance from the stationary tank. This 'semi-stationary' use greatly increases the range and convenience of the spraying system.

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENTS

Figure 1:
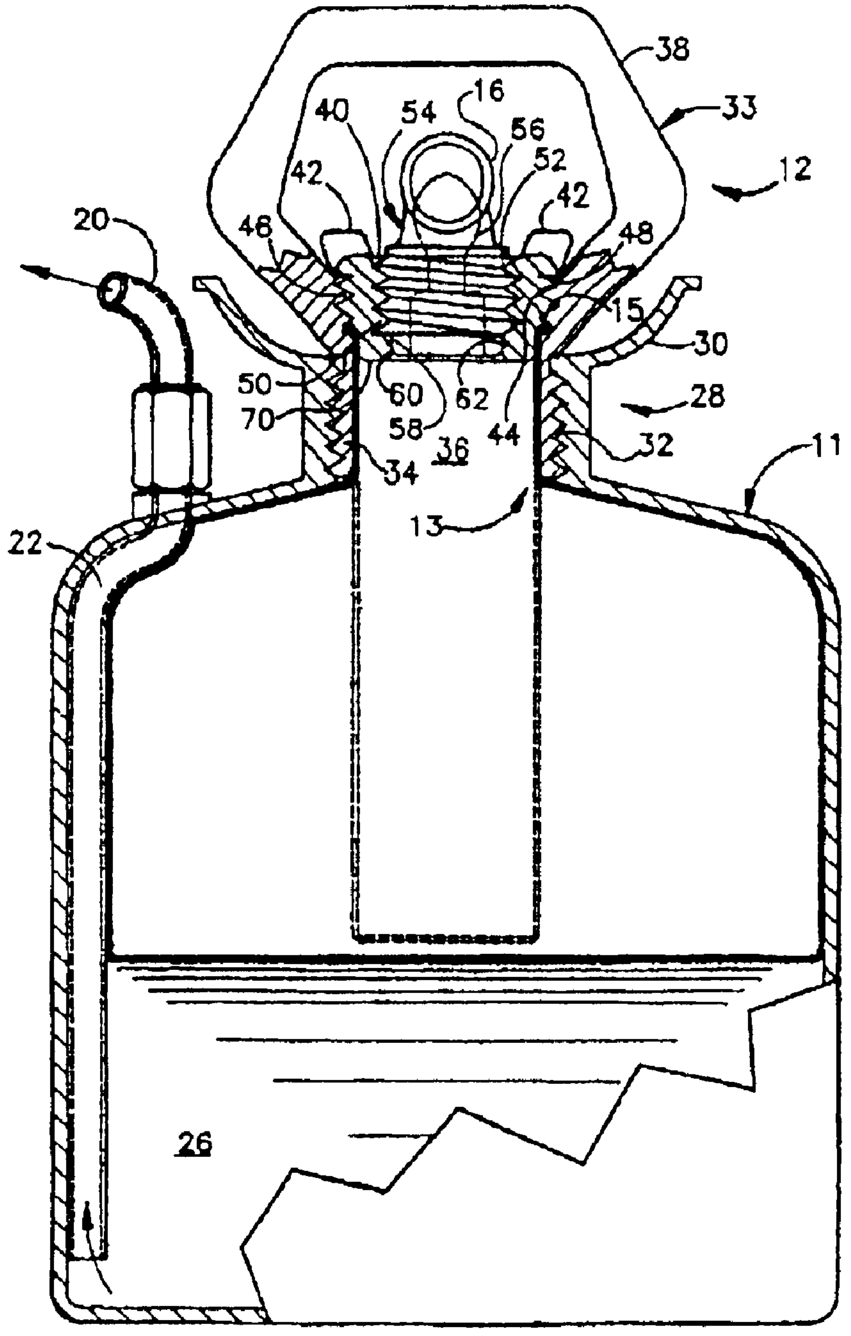
FIG. 1 (Prior Art)
FIG. 1 is a prior art dispensing tank 11 as disclosed in U.S. Pat. No. 5,398,852.

With reference to FIG. 1, there is shown the prior art dispensing tank 11 as disclosed in U.S. Pat. No. 5,398,852 to the present inventor. A spray hose 20 is connected to a spray hose fitting at one side of the tank. An internal pipe 22 is connected to the spray hose fitting and extends to the bottom of the tank to permit the liquid therein to enter the bottom of the internal pipe 22 to be dispensed.

The top of the tank has a large opening 28 made up of a funnel portion 30 and an internally threaded portion 32. The closure cap 12 of the '852 patent is screwed into the tank opening and consists of a threaded tank connector portion 34, a handle 38, and throat opening 36. A liquid tight flexible bladder 13 is secured to the tank connector portion 34 by the bladder neck ring portion 15 of a sealing plug 40. The bladder 13 is secured to the cap 12 by having the bladder neck ring captured between neck ring portion 15 of a sealing plug 40 and an internal shoulder of the handle assembly 38. The sealing plug 40 also has internal threads 50 adapted to mate with external threads 52 of hose connector assembly 54. The hose connector 54 has a hose fitting plug 16, a passageway 56 which connects a hose to the interior of the bladder 13 and a lower external smooth periphery 58 adapted to provide a close fit to a smooth internal surface 60 of the sealing plug 40. The internal surface 60 contains an O-ring seal 62 to enable a liquid tight seal between the hose connector assembly 54 and the sealing plug 40. When liquid is to be dispensed it is placed in the tank, the collapsed flexible bladder 13 is inserted through the main opening into the tank and is secured to the cap 12 by having the bladder neck ring captured between the neck ring portion 15 of a sealing plug 40 and an internal shoulder of the handle assembly 38. Next, the garden hose coupler 16 is connected with a standard garden hose which in turn is connected to a supply of pressurized water. The water flows through the coupling and passageway in the cap 12 to fill and inflate the flexible bladder 13 which expands against the liquid in the container. As the pressure builds the contents are dispensed through the hose and nozzle. The foregoing structure of the cap 12 resulted in a cumbersome attachment procedure of bladder 13. The present invention simplifies the bladder attachment structure and greatly increases the integrity thereof. Consequently, the spraying system is operable over a much broader range of pressures, and allows for easier and more reliable attachment of the bladder. The increased and sustained pressure capabilities of the present invention allow the use of a much longer spray hose 20, which in turn facilitates the use and sale of a portable spraying system in which the water-pressurized tank is positioned stationary on the ground at some convenient location and the hose-connected spray head can be carried around for more convenient wide-area spraying.

Figure 2:
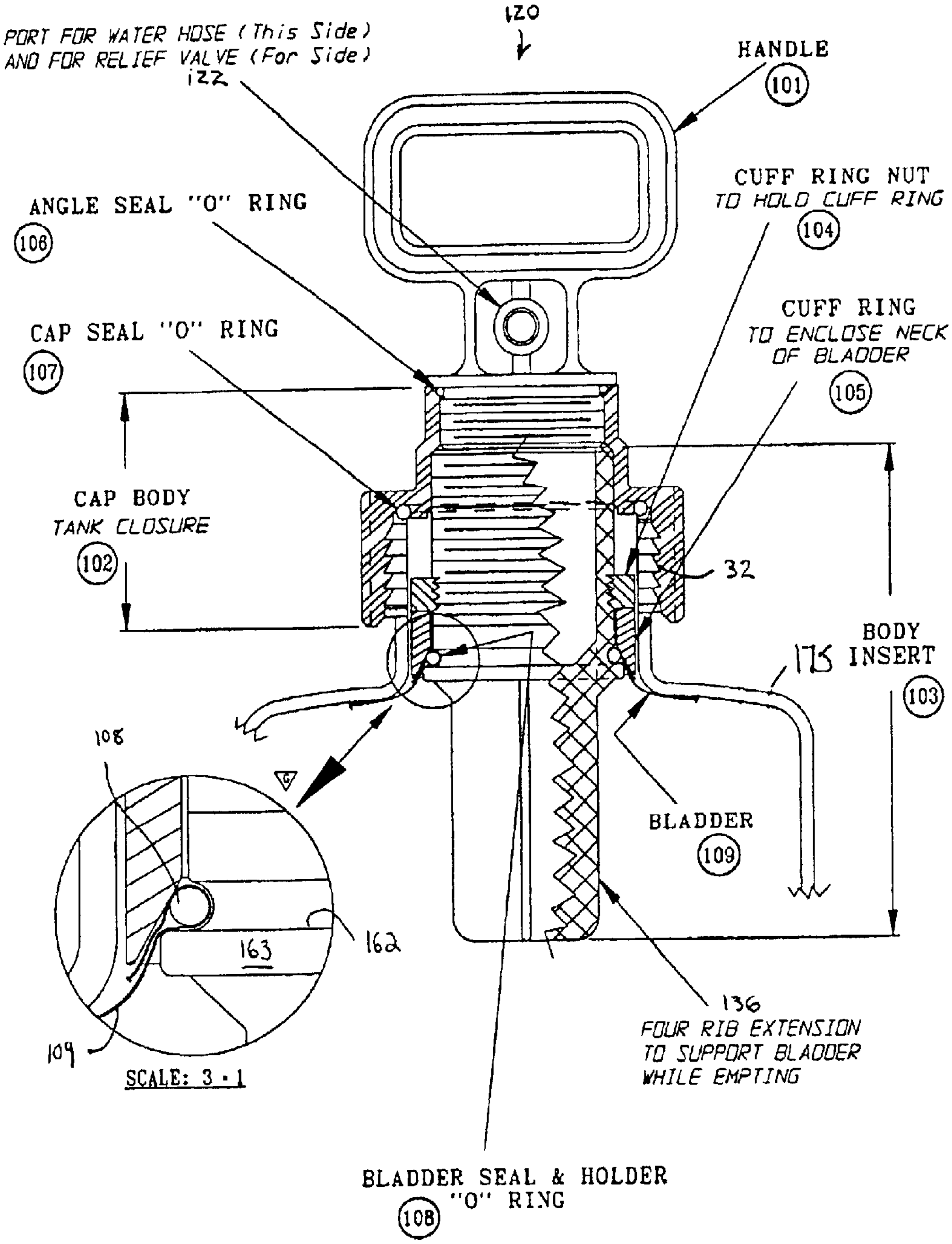
FIG. 2 is a cross-section of an improved cap assembly 120 according to the present invention.

FIG. 2 is a cross-section of an improved sprayer and cap assembly 120 according to the present invention with partial view of tank 175. The top of the tank 175 has a large opening circumscribed by an externally threaded portion 32. The cap assembly 120 in FIG. 2 is screwed over and into the tank opening by turning a handle assembly 101. The cap assembly 120 also includes a threaded cap body 102, a handle 101, and rib extension 136. A liquid tight flexible bladder 109 is secured to cap assembly 120 in a novel manner to be described and protrudes down into tank 175. A standard garden hose is connected to handle assembly 101 at a hose fitting plug 122. A vertical conduit 117 leads from the hose fitting plug 122 down through the cap assembly 120 and out through openings 138 in the ribbed extension 136 to the interior of the bladder 109 (see FIG. 8). The handle assembly 101 has an internal threaded lower section that mates with an external threaded neck in the top of cap body 102. Likewise, ribbed extension 136 has an external threaded upper section that mates with an internal threaded orifice in the bottom of cap body 102.

The structure of the cap assembly 120 will now be described in more detail, inclusive of the unique coupling assembly by which liquid tight flexible bladder 109 is secured to cap assembly 120.

Figure 3:
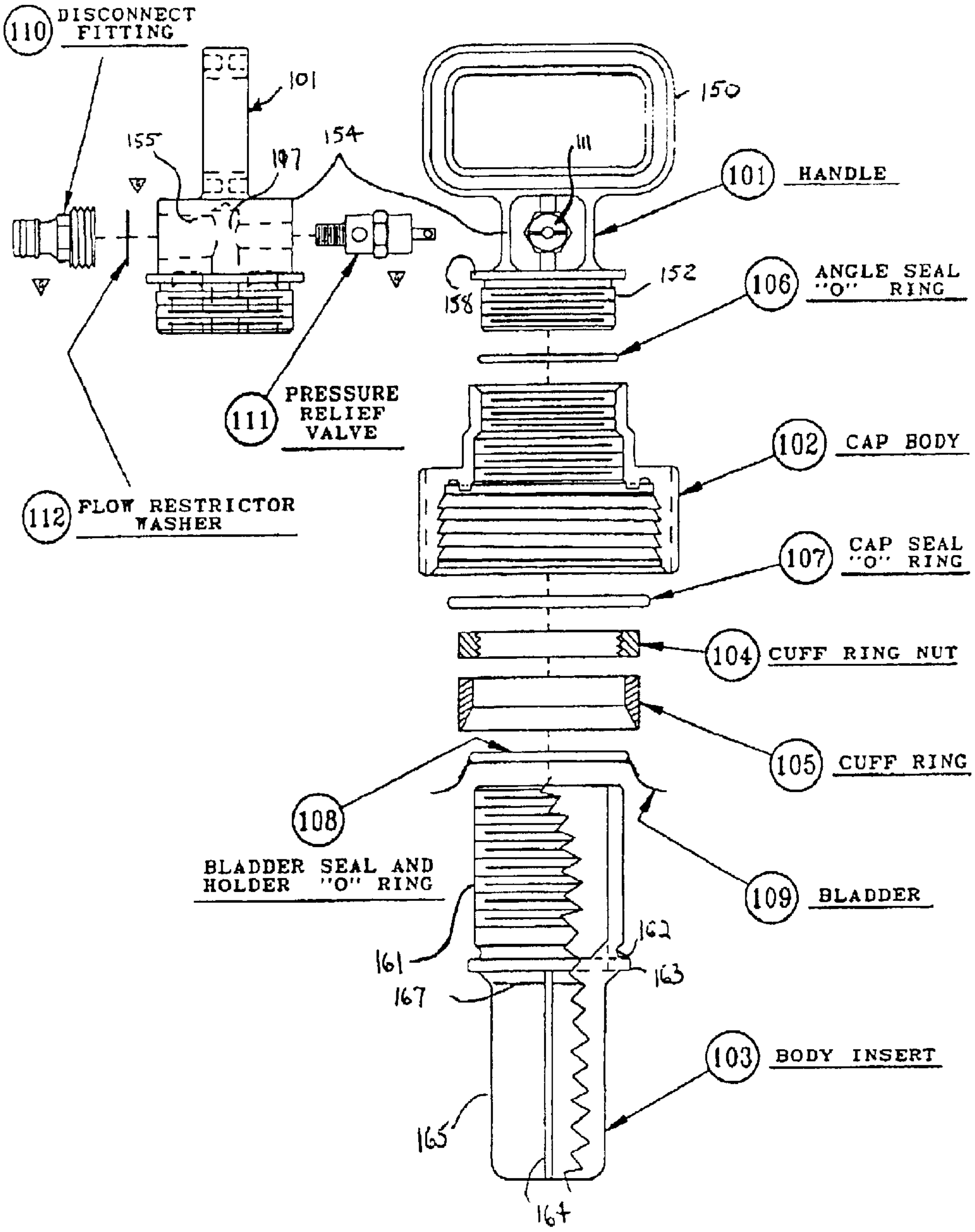
FIG. 3 is an exploded cross-section showing the discrete components of cap assembly 120 of FIG. 2.

FIG. 3 is an exploded cross-section showing the discrete components of cap assembly 120 according to the present invention. With combined reference to FIGS. 2 and 3, the handle 101 is preferably a molded component having a grip ring portion 150, a threaded lower portion 152 bordered by a flange 158, and a mid-section 154 defined by a threaded lateral channel 155. One end of threaded channel 155 is adapted for screw-insertion of a standard quick-disconnect fitting 110 for attachment of a water hose. The other end of threaded channel 155 is adapted for screw-insertion of a water pressure relief valve 111. The water pressure relief valve 111 is a standard check valve, and there are a variety of suitable commercially available components that will suffice. The handle 101 is also preferably molded with an internal vertical conduit 117 intersecting lateral channel 155. A conventional O-ring 106 is inserted onto the handle 101 around threaded lower portion 152 and abutting flange 158 to ensure a liquid tight seal. Handle 101 screws into the top aperture of a three-tier threaded cap body 102 as shown. The bottom of threaded cap body 102 flares outward to a larger internal threaded opening for screw attachment onto the tank, and a middle tier of internal threads is adapted for screw insertion of the body insert 103. Another conventional O-ring 107 is inserted into the bottom of threaded cap body 102 to ensure a liquid tight seal against the mouth of the tank 175. The body insert 103 is an extended tubular member having an upper threaded section 161 extending to a radial channel 162. Channel 162 is bounded on one side by a flange 163, and a discharge hose 167 points downward and away from the flange 163. An extended ribbed portion 165 of body insert 103 leads downward from discharge hose 167, and ribbed member 165 is intended to provide support for the rubber bladder when applying or removing same. The ribbed portion 165 may be, for instance, an X-shaped cross-section with flow ports 164. The bladder 109 is conveniently attached to the body insert 103 in the following manner. The mouth of the bladder 109 is inserted through a bladder seal O-ring 108, and the margins of the bladder 109 are doubled back around the outside of the bladder seal O-ring 108. The bladder 109 and bladder seal O-ring 108 are then stretched over the downwardly-extending ribbed portion 165 of body insert 103 and the bladder seal O-ring 108 is seated in the channel 162, thereby compression-fitting the mouth of the bladder 109 over flange 163. The security of the compression fitting is further increased by a radial cuff ring 105 which is inserted onto the threaded portion 161 of body insert 103. The radial cuff ring 105 has a smooth inner diameter sized to closely fit the body insert 103, and an outwardly tapered lower aperture designed to bias the mouth of the bladder 109 and bladder seal O-ring 108 downward and inward against the flange 163. A cuff ring nut 104 screws downward onto the threaded portion 161 of body insert 103 and against the radial cuff ring 105 to lock the mouth of the bladder 109/bladder seal O-ring 108 in place (see enlarged bubble illustration in FIG. 2).

Figure 4:
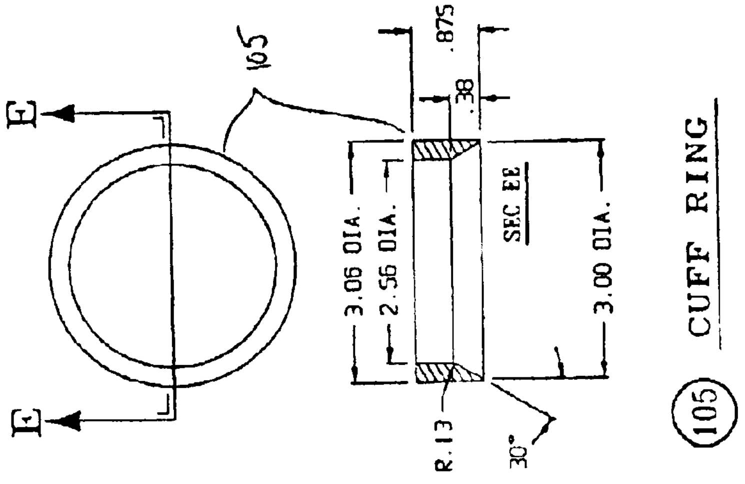
FIG. 4 is a composite top and cross-sectional view of the radial cuff ring 105.

FIG. 4 is a composite top and cross-sectional view of the radial cuff ring 105 showing the outwardly tapered lower aperture designed to bias the bladder seal O-ring 108 downward and inward.

Figure 5:
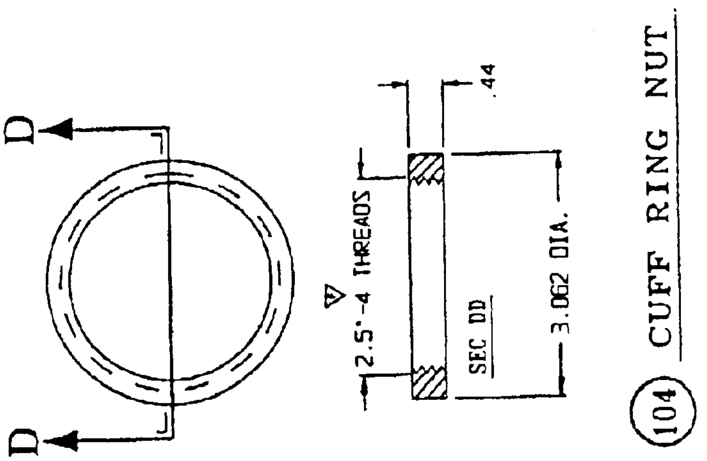
FIG. 5 is a composite top and cross-sectional view of the cuff ring nut 104.

FIG. 5 is a composite top and cross-sectional view of the cuff nut 104 which is internally-threaded to screw downward onto the threaded portion 161 of body insert 103 and against the radial cuff ring 105.

The forgoing configuration of the cap assembly 120 facilitates quick and convenient attachment of bladder 109. Moreover, the bladder attachment is far more stable and secure under pressure. Consequently, the spraying system is operable over a much broader range of pressures.

In operation of the foregoing sprayer, liquid is to be dispensed it is placed in the tank, the collapsed flexible bladder 109, which is attached to the cap assembly 120 as described above, is inserted through the main opening into the tank and the cap is screwed tight to the tank opening. Next, the garden hose quick-connect fitting 110 is connected with a similarly equipped quick-connect garden hose which in turn is connected to a supply of pressurized water. The water flows through the quick-connect fitting 110 and passageway 155 in the cap assembly 120 downward through the foregoing components and outward through discharge nozzle 167 to fill and inflate the flexible bladder 109 which expands against the liquid in the container. After the pressure builds the contents are dispensed through the spray discharge assembly 125 (see FIG. 9).

Figure 6:
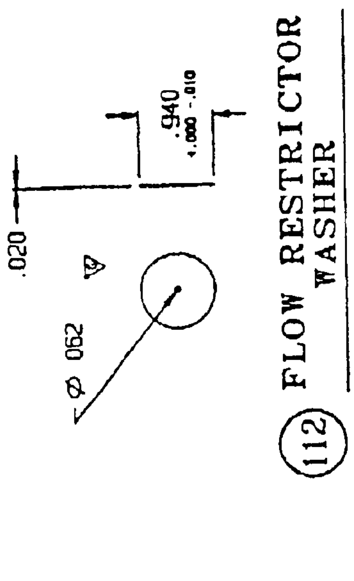
FIG. 6 is a composite top and side view of a flow restrictor orifice 112.

FIG. 6 is a composite top and side view of the flow restrictor orifice 112 which is used in conjunction with the relief valve 111 in the cap assembly 120 to limit the water flow rate from the garden hose to a level commensurate with requirements for correct spraying and tank protection from rupture. The flow restrictor orifice 112 comprises a circular disk sized to fit inside the threaded aperture of the handle assembly 101 (into which the quick-connect coupling 110 is screwed). The flow restrictor orifice 112 is formed with a central flow controlling orifice of a size calibrated in accordance with the maximum flow requirements of the user. Water systems vary greatly in their flow rate (gallons per minute), and sometimes the flow rate drives the cap assembly 120 to an excessive spray output. The inclusion of the flow restrictor orifice 112 between the hose quick-connect fitting 110 and inside handle assembly 101 limits the maximum gallons per minute yield from the garden hose to a flow rate that is more suitable for the task at hand, and which is lower than that of the cooperating relief valve 111. As a result, the tank is protected from rupture.

Figure 8:
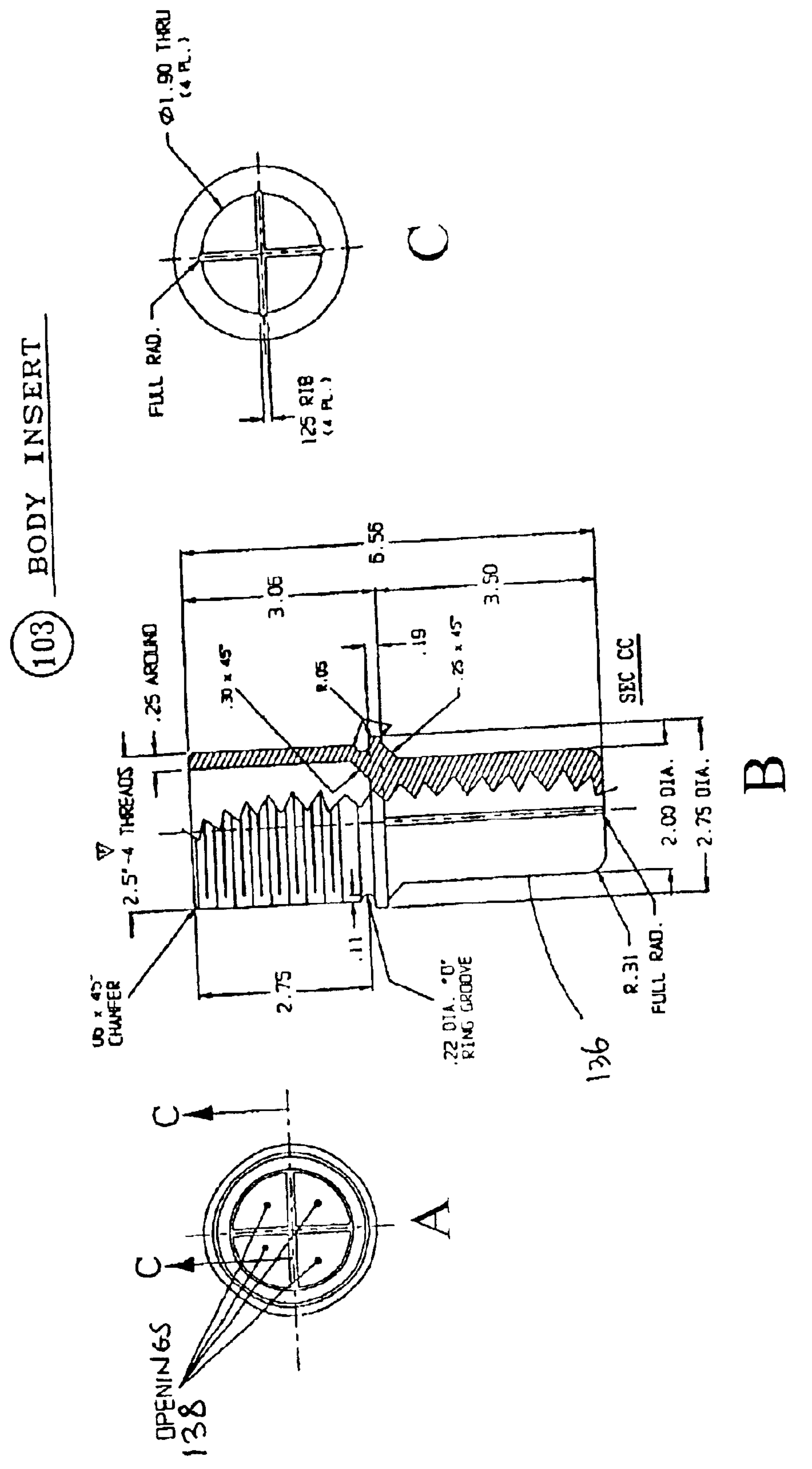
FIG. 8 displays openings 138 in the ribbed extension 136 of body insert 103 by which pressurized water supplied by a garden hose is discharged into the interior of bladder 109 as viewed in FIG. 2.

FIG. 8 displays openings 138 in the ribbed extension 136 of body insert 103 by which pressurized water supplied by a garden hose is discharged into the interior of bladder 109 (shown in FIG. 2).

Figure 9:
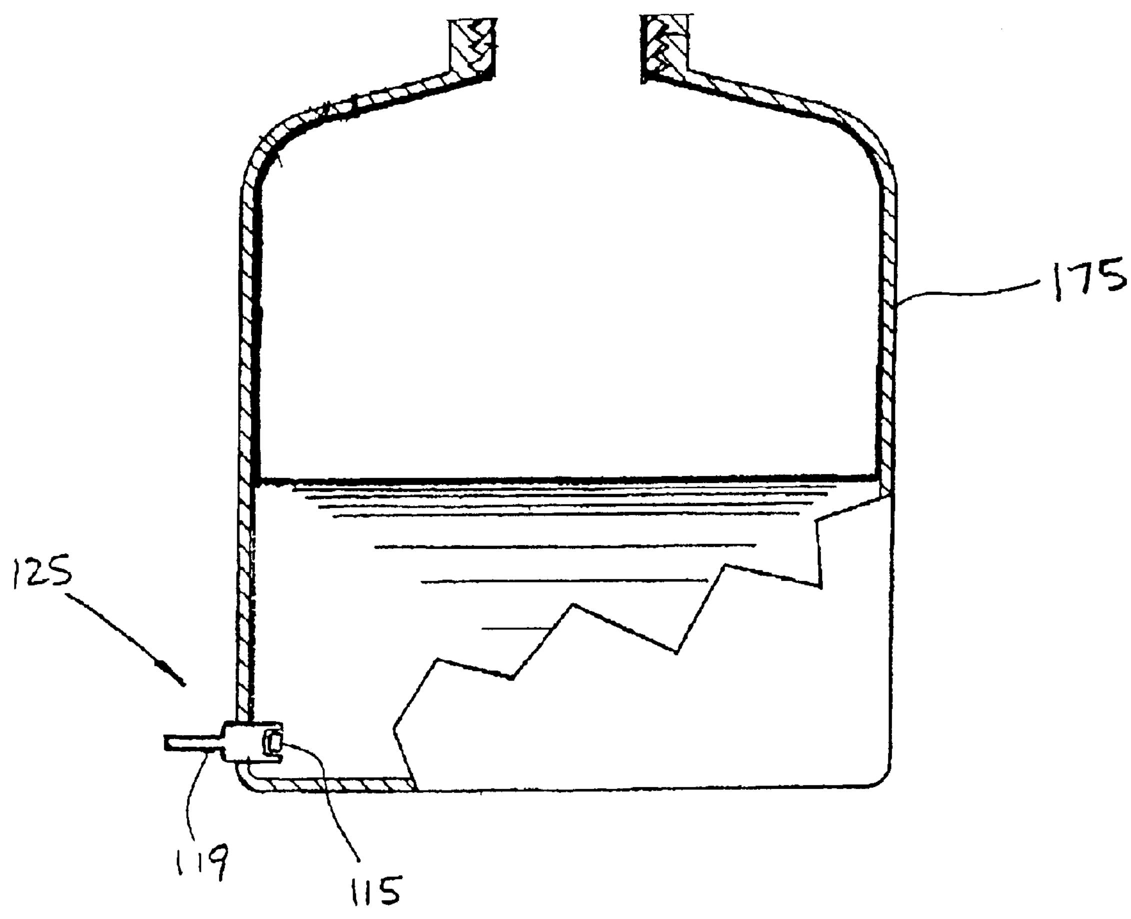
FIG. 9 illustrates the installation of the spray discharge assembly 125 in a tank 175.
Figure 10:
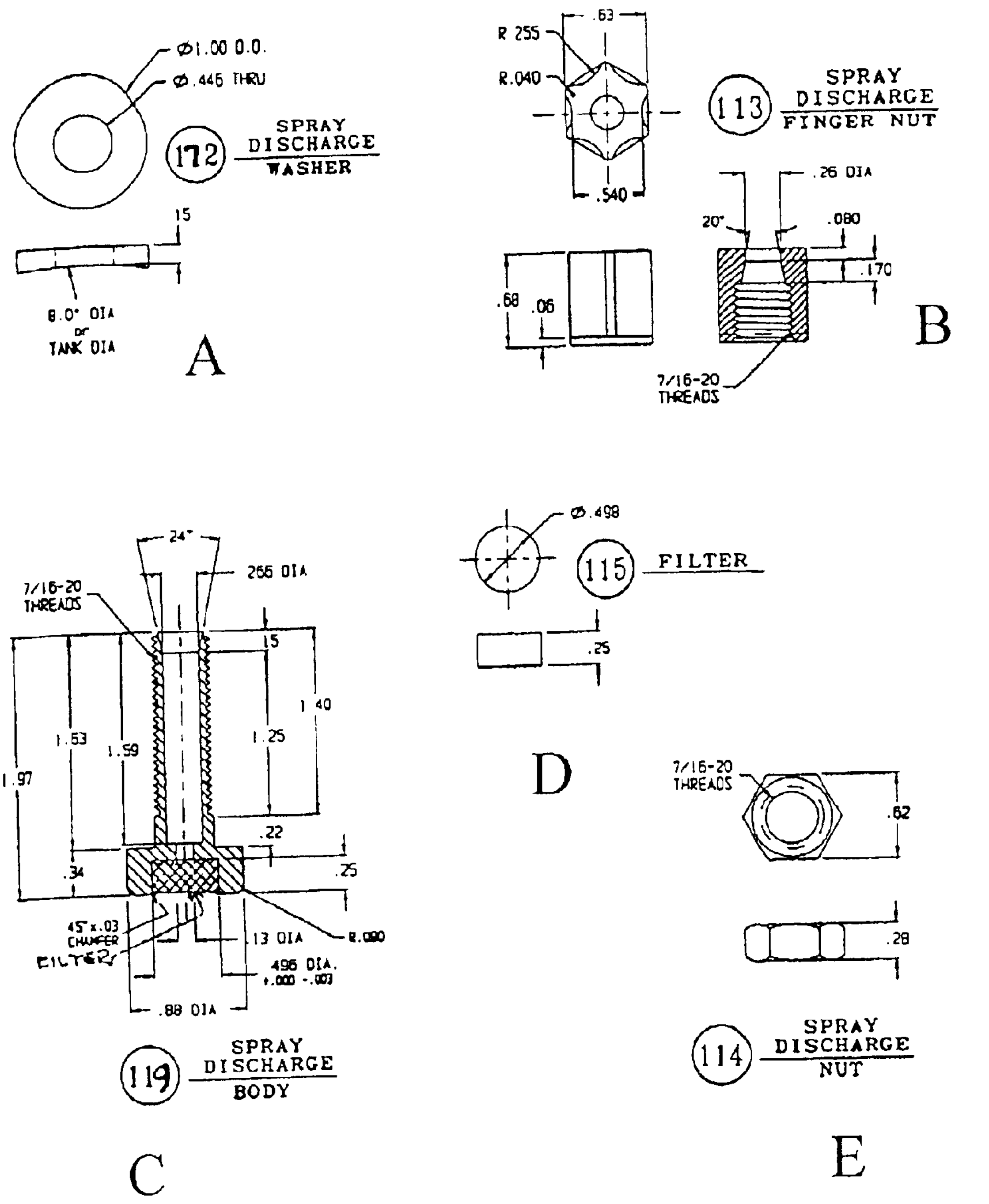
FIG. 10 illustrates the discrete components of the spray discharge assembly 125 including the body 119 and the protective porous filter 115.

FIG. 9 shows the manner in which the spray discharge assembly 125 is installed in the side wall of a tank 175 near its bottom and FIG. 10 details the discrete components of the spray discharge assembly 125, namely, a spray discharge body 119, filter 115, nut 114, washer 172, and finger nut 113. The spray discharge assembly 125 is positioned at one side of a tank 175 near the bottom (compare FIG. 1). A small (approx. ⅛" i.d.) spray hose 20 of 30' (+ or −) length may be connected to the spray discharge assembly 125 at the side of the tank. Preferably, the spray discharge assembly 125 incorporates a conventional porous mesh filter 115 to protect the bladder 109 from excessive stresses. The design of the spray discharge body 119 incorporates a 90 to 120 micron porous filter 115 to protect the bladder 109 from damage from excessive elongation stresses that would otherwise exceed its elastic limits. The design also permits easy replacement of said filter 115 as may be required.

FIG. 10 illustrates the discrete components of the spray discharge assembly 125 as in FIG. 9 including the body 119 and the protective porous filter 115 as described above.

Figure 11:
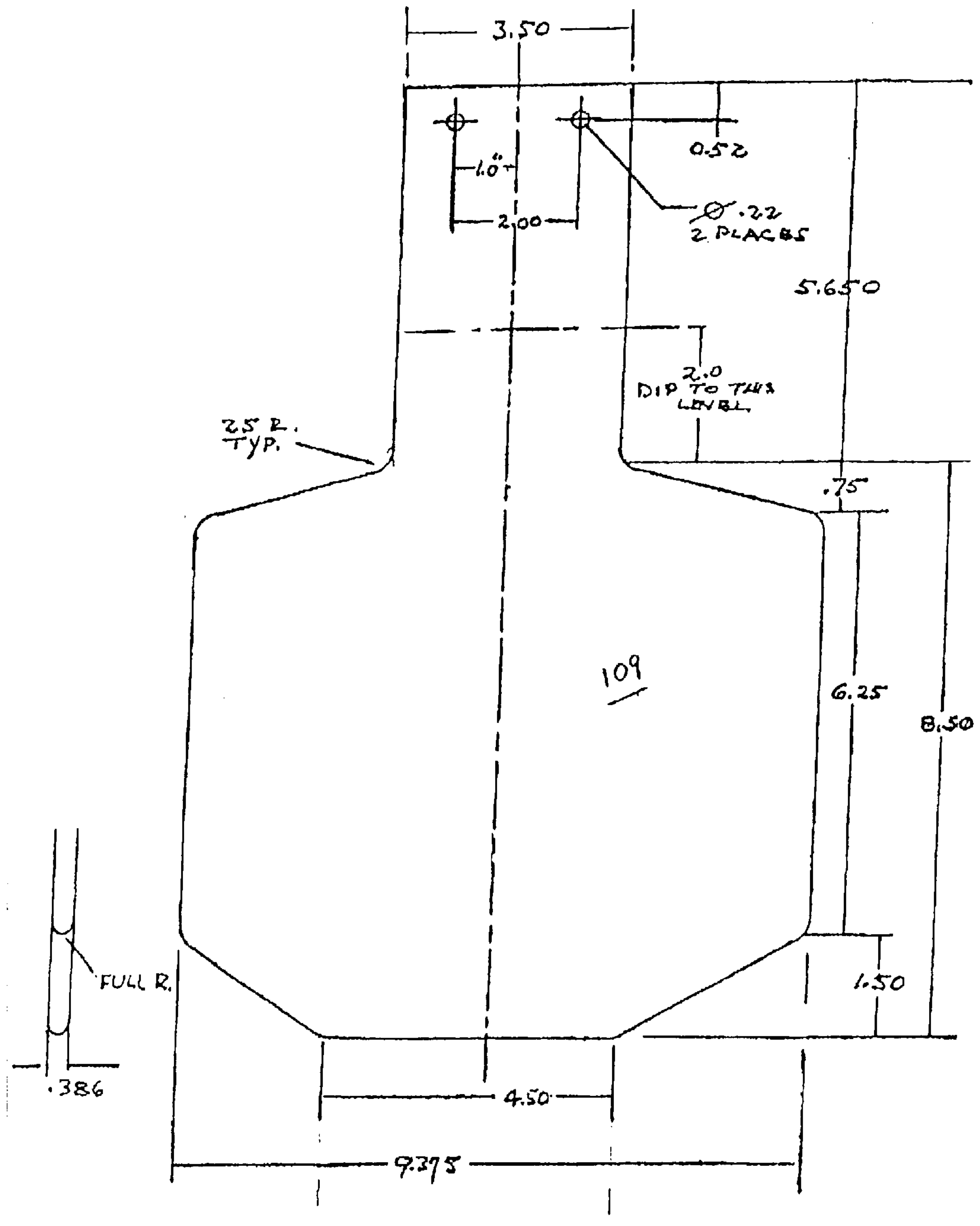
FIG. 11 is a composite front and side view of the flexible bladder 109.

FIG. 11 illustrates bladder 109 according to the present invention. Bladder 109 is a unitary molded member having a tapered configuration This tapered configuration of the bottom section of the bladder 109 provides for more uniform expansion within the tank, due to the inflow of pressurized water, without allowing any portion of the bladder 109 to block the spray discharge assembly 125 (see FIG. 9).

Figure 7:
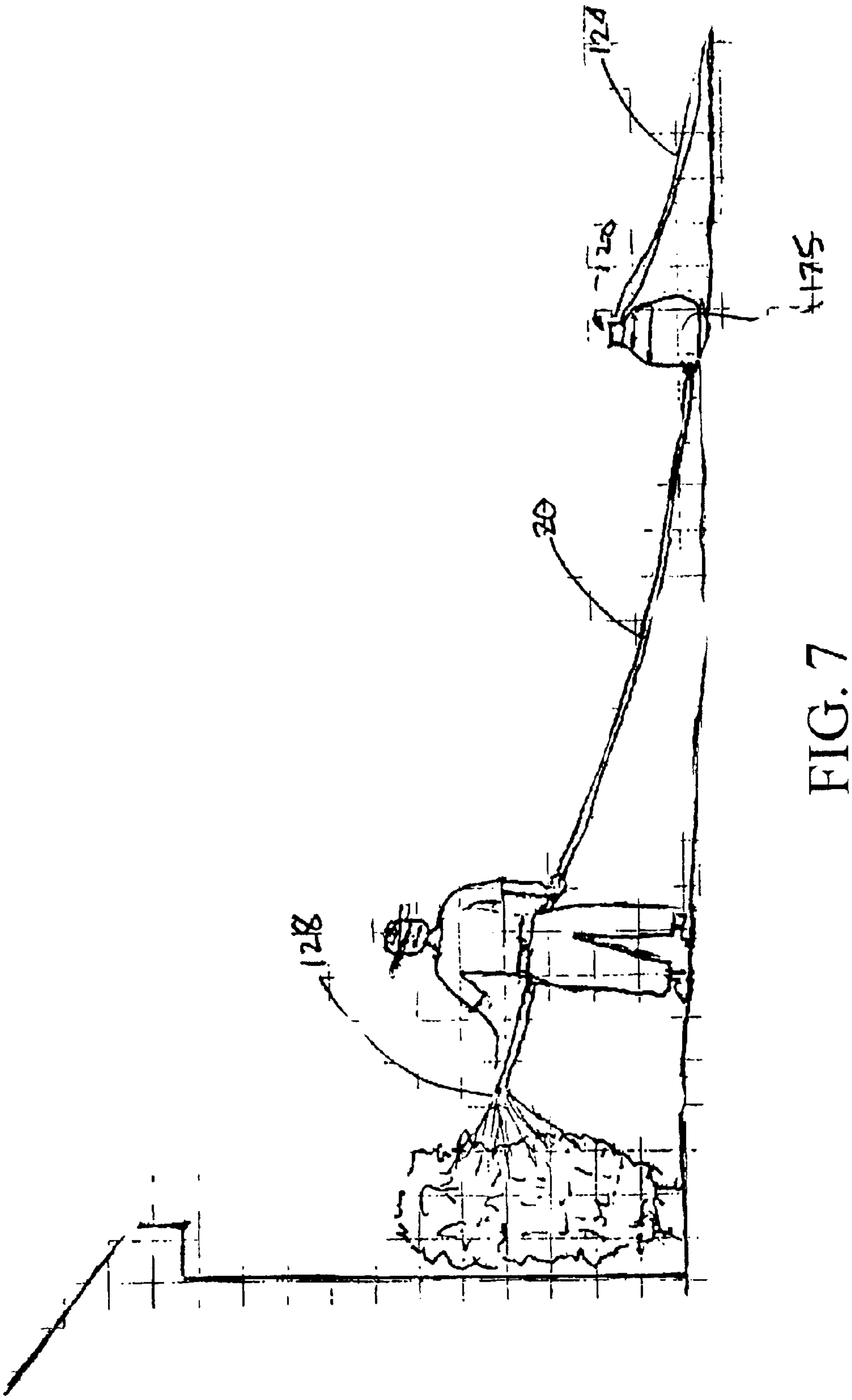
FIG. 7 illustrates the use of the present invention as a portable spraying system with a long, small diameter spray hose 20.

FIG. 7 illustrates another mode of operating the present device for remote and more convenient wide-area spraying. The liquid to be dispensed is placed in the tank, and the collapsed flexible bladder 109, which is attached to the cap assembly 120 as described above, is inserted through the main opening into the tank and the cap is screwed tight to the tank opening. The water-pressurized tank 175 is placed stationary on the ground and a long spray hose 20 is used, thereby making the hose-connected spray head 128 more remote for convenient wide-area spraying. In this regard, FIG. 7 depicts the use of a 30' (+ or −) spray hose 20 which results in a highly portable spraying system. The user attaches the garden hose 124 to the cap assembly 120 and this gives a range equal to the length of the garden hose 124 which may be up to 100 feet. Rather than carrying the spraying system, the user places the tank 175 at a fixed position on the ground and then attaches an elongated spray hose 20. The spray hose 20 can be uncoiled and used remotely, and this adds another 30' (+ or −) to the system's range. Moreover, using the spraying system in this manner eliminates carrying the bulk of the tank 175 while spraying. Thus, the foregoing method of using the spraying system makes it suitable for home and garden use. Since the spraying system frees the operator from both carrying the tank 175 and pumping, it satisfies the special needs of older or partially handicapped gardeners and reduces the labor for all users.

The foregoing sprayer improves upon the concept shown in the present inventors U.S. Pat. No. 5,398,852 patent with structural improvements in the water-pressurized base for greater suitability to task, and specifically an improved bladder retaining neck structure as well as a pressure-limiting O-ring to compensate for water systems of varying pressures. Moreover, the base is suitable for use as a stationary base with remote hose-connected spray head for more convenient wide-area spraying.

Having now fully set forth the preferred embodiments and certain modifications of the concept underlying the present invention, various other embodiments as well as certain variations and modifications of the embodiments herein shown and described will obviously occur to those to those skilled in the art upon becoming familiar with said underlying concept. It is to be understood, therefore, that the invention may be practiced otherwise than as specifically set forth in the appended claims.

I claim:

1. A liquid spraying system comprising:

a tank reservoir having a spray discharge assembly attached thereto for spraying contents of said tank reservoir;

a cap assembly for attachment to said tank reservoir, said cap assembly further comprising, a cap body for attachment to said tank reservoir, a handle assembly for attachment to said cap body, said handle assembly including a first aperture for attachment of a water hose and a second aperture for attachment of a relief valve;

a body insert for attachment to said cap body, said body insert having an annular flange and an annular groove adjacent to said flange, and a flexible bladder for attachment to said body insert by seating a lip of said bladder over the flange and in the annular groove of said body insert, and a cap body for screw-attachment to said tank reservoir.

2. The liquid spraying system according to claim 1, further comprising a bladder seal O-ring for wrapping a mouth of said bladder thereabout and adapted to be seated in said groove of said body insert against said flange to facilitate attachment of said bladder to said body insert.

3. The liquid spraying system according to claim 1, wherein said spray discharge assembly is positioned at the side of the tank reservoir near the bottom.

4. The liquid spraying system according to claim 3, wherein said spray discharge assembly includes a porous filter.

5. The liquid spraying system according to claim 4, wherein said bladder is tapered at its distal end such that said contents of said tank reservoir are discharged through said spray discharge assembly and said sprayer hose without allowing any part of said bladder to come into contact with said filter and block the flow of said contents through said spray discharge assembly and said sprayer hose.

6. The liquid spraying system according to claim 1, wherein said cap assembly further comprises a cuff ring around said body insert for exerting a clamping force on said bladder seal O-ring and a cuff ring nut threaded onto said body insert tightenable against said cuff ring for clamping said bladder seal O-ring and said bladder in place.

7. The liquid spraying system according to claim 6, wherein said cuff ring comprises an outwardly tapered lower aperture for exerting a downward and inwardly directed clamping force on said bladder seal O-ring and said bladder.

8. The liquid spraying system according to claim 1, wherein said cap assembly further comprises a flow restrictor orifice coupled to one of said lateral apertures of said handle assembly, and a relief valve coupled to another of said lateral apertures of said handle assembly, said flow restrictor orifice and said relief valve combining to protect said tank reservoir from excessive internal pressure.

9. The liquid spraying system according to claim 1, wherein said handle assembly further comprises an upper portion in the form of a grip ring.

10. The liquid spraying system according to claim 1, wherein said lower portion of said handle assembly further comprises an annular flange such that a liquid-tight seal is created when an O-ring seal is inserted between said lower portion of said handle assembly and said cap body.

11. A unitary pressurizing tank closure for a liquid spraying system comprising:

a cap body for screw-attachment to a tank reservoir, a handle assembly having a lower portion for attachment to said cap body, and lateral apertures for attachment of a water hose and a relief valve;

a body insert for attachment to said cap body, said body insert having an annular flange and groove adjacent said flange, a bladder for attachment to said body insert, and a bladder seal O-ring for wrapping a mouth of said bladder thereabout and adapted to be seated in said groove of said body insert against said flange to facilitate attachment of said bladder to said body insert.

12. The unitary pressurizing tank closure according to claim 11, further comprising a cuff ring around said body insert for exerting a clamping force on said bladder seal O-ring and a cuff ring nut threaded onto said body insert tightenable against said cuff ring for clamping said bladder seal O-ring and said bladder in place.

13. The unitary pressurizing tank closure according to claim 12, wherein said cuff ring comprises an outwardly tapered lower aperture for exerting a downward and inwardly directed clamping force on said bladder seal O-ring and said bladder.

14. The unitary pressurizing tank closure according to claim 11, further comprising a flow restrictor orifice coupled to one of said lateral apertures of said handle assembly, and a relief valve coupled to another of said lateral apertures of said handle assembly, said flow restrictor orifice and said relief valve combining to protect said tank reservoir from excessive internal pressure.

15. The unitary pressurizing tank closure according to claim 11, wherein said handle assembly further comprises an upper portion in the form of a grip ring.

16. The unitary pressurizing tank closure according to claim 11, wherein said lower portion of said handle assembly further comprises an annular flange such that a liquid-tight seal is created when an O-ring seal is inserted between said lower portion of said handle assembly and said cap body.

* * * * *